United States Patent
Hamm

(10) Patent No.: US 12,420,053 B2
(45) Date of Patent: Sep. 23, 2025

(54) LAYERED YARN AND WEIGHTED BLANKET FOR DEEP PRESSURE THERAPY

(71) Applicant: Bearaby Inc., Wilmington, DE (US)

(72) Inventor: Kathrin Hamm, New York, NY (US)

(73) Assignee: Beraby Inc., Brooklyn, NY (US)

( * ) Notice: Subject to any disclaimer, the term of this patent is extended or adjusted under 35 U.S.C. 154(b) by 0 days.

(21) Appl. No.: 18/384,476

(22) Filed: Oct. 27, 2023

(65) Prior Publication Data

US 2024/0058567 A1    Feb. 22, 2024

Related U.S. Application Data

(63) Continuation of application No. 17/650,147, filed on Feb. 7, 2022, now Pat. No. 11,806,480, which is a
(Continued)

(51) Int. Cl.
*A61M 21/02*    (2006.01)
*D04B 1/22*    (2006.01)
(Continued)

(52) U.S. Cl.
CPC .............. *A61M 21/02* (2013.01); *D04B 1/22* (2013.01); *D04B 21/20* (2013.01); *D04B 31/00* (2013.01);
(Continued)

(58) Field of Classification Search
CPC . A61M 21/02; A61M 2021/0022; D04B 1/22; D04B 1/225; D04B 21/20; D04B 31/00; D10B 2509/00
See application file for complete search history.

(56) References Cited

U.S. PATENT DOCUMENTS

| 429,894 A | 6/1890 | Doremus |
| 1,365,731 A * | 1/1921 | Schloss .................. A41F 17/00 2/273 |

(Continued)

FOREIGN PATENT DOCUMENTS

| AU | 2008100762 A4 | 9/2008 |
| CN | 202407217 U | 9/2012 |

(Continued)

OTHER PUBLICATIONS

Ohhio Braid Unique Chunky Creation, Kickstarter, https:/Avww. kickstarter.com/projects/1163965827/ohhio-braid-unique-craft-material-for-chunky-creat/description, image retrieved by Wayback Machine Dec. 29, 2016. (Year: 2016).*

(Continued)

*Primary Examiner* — Fredrick C Conley
(74) *Attorney, Agent, or Firm* — Key Kesan Dallmann, PLLC

(57) ABSTRACT

Disclosed is a weighted material that is configured to effectuate deep pressure therapy to a person when the weighted material is used as a blanket over the person's body. A length of layered yarn is interlooped to form the weighted material. The layered yarn includes an outer tube extending longitudinally from a first end to a second end. The outer tube defines a conduit extending longitudinally therethrough from the first end to the second end. A fiber material is disposed within the conduit and extend longitudinally from the first end to the second end. The interlooped length of yarn, by itself, is configured and sufficiently weighted to effectuate deep pressure therapy to a person when the blanket lies over the person's body. Various other systems and methods are also disclosed.

28 Claims, 7 Drawing Sheets

Related U.S. Application Data continuation of application No. 17/099,033, filed on Nov. 16, 2020, now Pat. No. 11,260,199, which is a continuation of application No. 16/193,792, filed on Nov. 16, 2018, now Pat. No. 10,835,708.

(51) Int. Cl.
*D04B 21/20* (2006.01)
*D04B 31/00* (2006.01)
*G01N 33/50* (2006.01)
*A61M 21/00* (2006.01)

(52) U.S. Cl.
CPC . *G01N 33/5088* (2013.01); *A61M 2021/0022* (2013.01); *D10B 2509/00* (2013.01)

(56) References Cited

U.S. PATENT DOCUMENTS

| | | | |
|---|---|---|---|
| 2,339,950 A | 1/1944 | Sackner | |
| 2,372,263 A | 3/1945 | Eudy | |
| 2,425,293 A | 8/1947 | McDermott | |
| 2,526,738 A | 10/1950 | Finlayson et al. | |
| 2,570,012 A | 10/1951 | Temple | |
| 2,593,589 A | 4/1952 | McIntyre | |
| 2,715,086 A | 8/1955 | Frederick | |
| 3,596,459 A | 8/1971 | Wada et al. | |
| 4,052,238 A | 10/1977 | Botvin | |
| 4,191,221 A * | 3/1980 | Boyer | D03D 15/47 139/426 R |
| 4,263,777 A | 4/1981 | Wada et al. | |
| 4,343,334 A | 8/1982 | Schulze et al. | |
| 4,437,422 A | 3/1984 | Torres | |
| 4,479,270 A | 10/1984 | Novinger | |
| 4,588,635 A | 5/1986 | Donovan | |
| 4,634,618 A | 1/1987 | Greer et al. | |
| 4,664,160 A | 5/1987 | Rothstein et al. | |
| 4,797,311 A | 1/1989 | Kemp | |
| 4,839,934 A * | 6/1989 | Rojas | A47G 9/0207 5/486 |
| 4,910,855 A | 3/1990 | Balarzs | |
| 4,958,663 A | 9/1990 | Miller et al. | |
| 5,198,288 A | 3/1993 | Grunfeld | |
| 5,397,612 A | 3/1995 | Small et al. | |
| 5,603,514 A | 2/1997 | Jencks et al. | |
| 5,860,350 A | 1/1999 | Rexroad | |
| 6,015,618 A | 1/2000 | Orima | |
| 6,235,391 B1 | 5/2001 | Contreras et al. | |
| 6,240,716 B1 | 6/2001 | Yanagawase et al. | |
| 6,272,966 B1 * | 8/2001 | Montle | D04C 1/12 87/6 |
| 6,440,556 B2 | 8/2002 | Matsui et al. | |
| 6,493,910 B1 | 12/2002 | Dischler | |
| 7,870,623 B2 | 1/2011 | Judd | |
| 9,732,448 B2 | 8/2017 | Liu | |
| 9,834,873 B2 | 12/2017 | Nelis et al. | |
| 9,956,129 B2 | 5/2018 | Kjell | |
| 10,100,444 B2 | 10/2018 | Hamaguchi et al. | |
| 10,316,442 B2 | 6/2019 | Hamaguchi et al. | |
| 10,835,708 B2 | 11/2020 | Hamm | |
| 10,974,018 B2 * | 4/2021 | Pacheco | A47G 9/007 |
| 11,013,884 B2 | 5/2021 | Russin, Sr. et al. | |
| 11,051,639 B1 | 7/2021 | Nagy | |
| 11,260,199 B2 | 3/2022 | Hamm | |
| 11,806,480 B2 | 11/2023 | Hamm | |
| 2001/0053646 A1 | 12/2001 | Tanaka et al. | |
| 2006/0135021 A1 | 6/2006 | Calhoun et al. | |
| 2006/0174410 A1 | 8/2006 | Mastandrea, Jr. | |
| 2006/0185343 A1 | 8/2006 | Coombs | |
| 2006/0200906 A1 * | 9/2006 | Deering | A47G 9/1045 5/482 |
| 2007/0196420 A1 | 8/2007 | Dwyer | |
| 2009/0000264 A1 | 1/2009 | Ueda | |
| 2009/0100568 A1 * | 4/2009 | Judd | A63B 21/4025 112/475.08 |
| 2010/0263153 A1 | 10/2010 | Patrick et al. | |
| 2011/0047698 A1 | 3/2011 | Parker | |
| 2011/0119921 A1 | 5/2011 | Lewis | |
| 2011/0274903 A1 | 11/2011 | Stuart et al. | |
| 2012/0186014 A1 | 7/2012 | Shattuck et al. | |
| 2013/0295812 A1 * | 11/2013 | Lee | D04B 1/22 66/196 |
| 2014/0209098 A1 | 7/2014 | Dunn et al. | |
| 2014/0213421 A1 | 7/2014 | Paris | |
| 2014/0308865 A1 | 10/2014 | Kumar et al. | |
| 2015/0284886 A1 | 10/2015 | Ohtani et al. | |
| 2015/0366734 A1 | 12/2015 | Kjell | |
| 2016/0037944 A1 | 2/2016 | Savignano | |
| 2016/0108564 A1 | 4/2016 | Topolkaraev et al. | |
| 2016/0168767 A1 | 6/2016 | Bader et al. | |
| 2016/0265146 A1 * | 9/2016 | Liao | D04B 1/18 |
| 2017/0295887 A1 | 10/2017 | Torres et al. | |
| 2018/0035832 A1 | 2/2018 | Ureten | |
| 2018/0103783 A1 * | 4/2018 | Danaher | D03D 13/008 |
| 2018/0245249 A1 | 8/2018 | Yenici | |
| 2018/0305845 A1 * | 10/2018 | Sençopur | D04B 1/22 |
| 2018/0305847 A1 | 10/2018 | Wen et al. | |
| 2019/0021525 A1 | 1/2019 | Hamm | |
| 2019/0030392 A1 | 1/2019 | Skerjanz | |
| 2020/0238045 A1 | 7/2020 | Pacheco | |
| 2021/0180223 A1 | 6/2021 | Marynenko | |
| 2021/0180233 A1 | 6/2021 | Park et al. | |
| 2022/0330728 A1 * | 10/2022 | Beauregard | D02G 3/22 |
| 2022/0333072 A1 | 10/2022 | Trzonkowski et al. | |

FOREIGN PATENT DOCUMENTS

| | | |
|---|---|---|
| CN | 105755624 A | 7/2016 |
| CN | 206866730 U | 1/2018 |
| CN | 208640240 U | 3/2019 |
| DE | 19828218 A1 | 12/1999 |
| EP | 0249074 A2 | 12/1987 |
| EP | 0317523 A1 | 5/1989 |
| EP | 0201114 B1 | 7/1990 |
| EP | 1518951 A2 | 3/2005 |
| GB | 1051081 | 3/1965 |
| GB | 1285505 A | 8/1972 |
| JP | H09296332 A | 11/1997 |
| JP | 2013072154 A | 4/2013 |
| RU | 2113565 C1 | 6/1998 |
| WO | 2014116163 A1 | 7/2014 |
| WO | 2014166556 A1 | 10/2014 |
| WO | 2015144186 A1 | 10/2015 |
| WO | 2018013025 A1 | 1/2018 |
| WO | 2018111213 A1 | 6/2018 |
| WO | 2019177523 A1 | 9/2019 |
| WO | 2019237410 A1 | 12/2019 |

OTHER PUBLICATIONS

AE Sewing Machines, "ASA-MO6804S/RPSK Rouleau/Spaghetti Machine", Mar. 1, 2019, https://www.youtube.com/watch?v=fDULsqhvOvc, 1 page.

Blown Yarns: Are they any good? http://yarnsub.com:80/articles/texture/blown-yarns, retrieved by Wayback Machine Mar. 11, 2016 (5 pages).

Sheltered Co., "Breathable, Sustainable Weighted Blankets", Nov. 1, 2018, https://www.kickstarter.com/projects/1831123737/sheltered-co-breathable-sustainable-weighted-blank/description, 23 pages.

Surucu Apere, "C201 Overlok Spagetti Aperesi", Sep. 6, 2016, https://www.youtube.com/watch?v=Ylfb9ymNEx8, 1 page.

Knit Safari, "Chunky Knitting Patterns", Retrieved Dec. 22, 2021, Available online at https://www.knitsafari.com/collections/chunky-knitting-patterns, 11 pages.

Nocturnal Knits, "Giganto-Blanket FAQ", Available online at https://nocturnalknits.com/giganto-blanket-faq/, Oct. 17, 2011, 81 pages.

Ohhio, "Gorgeous chunky knits", Nov. 18, 2015, https://www.kickstarter.com/projects/1163965827/ohhio-gorgeous-chunky-knits/description, 34 pages.

Ohhio, "How to Arm Knit a Medium Ohhio Throw Using Braid", Nov. 15, 2016, https://www.youtube.com/watch?v=wbXk0-UoziA, 1 page.

(56) References Cited

OTHER PUBLICATIONS

Mama in a Stitch, "How To Easily Knit A Big Yarn Blanket", published Sep. 14, 2018, Retrieved Dec. 22, 2021, Available online at https://www.lionbrand.com/products/knit-kit-yooge-big-knit-blanket, 33 pages.
Mama in a Stitch, "How To Make A Big Knit Blanket", published Sep. 14, 2018, Retrieved Dec. 22, 2021, Available online at https://www.youtube.com/watch?v=s4RQqPmv6q0, 1 page.
Red Heart Design Team, Introducing Red Heart Strata Yarn, https://www.yarnspirations.com/blogs/community/rh-20160907-introducing-red-heart-strata-yarn, Sep. 7, 2016 (5 pages).
Lion Brand Yarn, Knit Kit, "Yooge Big Knit Blanket", Retrieved Dec. 22, 2021, Available online at https://www.lionbrand.com/products/knit-kit-yooge-big-knit-blanket, 6 pages.
Knitting with Rope: Knitting, eHow, https://www.youtube.com/watch?v=FKw-pjwaXz8, 2012 (3 pages).
Ohhio, "Large Ohhio Blanket", Available online at https://ohhio.com, Accessed from Internet on Oct. 29, 2018, 1 page.
Lion Brand Yarn, "Yooge Yarn", Retrieved Dec. 22, 2021, Available online at https://www.lionbrand.com/collections/yarn-weight-7-jumbo/products/lb-collection-yooge-yarn?variant=32421644370013, 6 pages.
Linda Dean Crochet, Knitted Yarn that Allows Crochet Stitches to Shine, www.lindadeancrochet.com/blog/?p=1328, posted Aug. 5, 2016 (5 pages).
Notknot Cushion by Umemi, https://homeli.co.uk/notknot-cushions-by-umemi-knitted-wool-rope-knot-pillows-on-vokuro/, archive by Wayback Machine Mar. 7, 2015 (9 pages).
Ohhio Braid Unique Chunky Creations, Kickstarter, https://www.kickstarter.com/projects/1163965827/ohhio-braid-unique-craft-material-for-chunky-creat/description, image retrieved by Wayback Machine Dec. 29, 2016 (27 pages).
Kicktraq, "Ohhio Braid/Unique Craft Material for Chunky Creations", Available online at https://www.kicktraq.com/projects/1163965827/ohhio-braid-unique-craft-material-for-chunky-creat/, Dec. 22, 2021, 5 pages.
Phat Knits, Redazione Area, https://www.area-arch.it/en/phat-knits, Sep. 14, 2014 (3 pages).
TMS, "Spaghetti Folder", Feb. 19, 2017, https://www.youtube.com/watch?v=IDq1Dye1fmg, 1 page.
Imagine Childhood, Spring Finger Knitting Project, https://blog.imaginechildhood.com/imagine-childhood/2011/04/-blue-knit-basket.html, Apr. 2011 (3 pages).
Swan, Orange, The Knitting Needle and the Damage Done: Phat Knits, http://theknittingneedleandthedamagedone.blogspot.com/2013/08/phat-knits.html, Aug. 2, 2013 (8 pages).
Yankovich, "These Giant Knitted Blankets are the Answer to Your Winter Prayers", Buzzfeed, Available online at https://www.buzzfeed.com/gyanyankovich/talk-about-a-chunky-knit, Jun. 15, 2015, 10 pages.
Sheltered Co., "Weighted Blanket Photo: Production Prototype", May 18, 2018, https://www.kickstarter.com/projects/1831123737/sheltered-co-breathable-sustainable-weighted/blank#prototype-slide-137692, 1 page.
Yarn 101: Strata By Red Heart, Episode 354, https://www.youtube.com/watch?v=R6Mx4Xfl4_8, posted Nov. 7, 2016 (4 pages).
U.S. Appl. No. 16/079,365, Non-Final Office Action dated Jan. 11, 2022, 8 pages.
U.S. Appl. No. 16/079,365, Final Office Action dated Jun. 16, 2022, 10 pages.
U.S. Appl. No. 16/193,792, Non-Final Office Action dated May 21, 2020, 7 pages.
U.S. Appl. No. 16/193,792, Notice of Allowance dated Sep. 17, 2020, 8 pages.
U.S. Appl. No. 17/099,033, Corrected Notice of Allowability dated Jan. 26, 2022, 2 pages.
U.S. Appl. No. 17/099,033, Notice of Allowance dated Oct. 28, 2021, 8 pages.
U.S. Appl. No. 17/650,147, Non-Final Office Action dated Feb. 28, 2023, 9 pages.
U.S. Appl. No. 17/650,147, Notice of Allowance dated Jan. 6, 2023, 8 pages.
U.S. Appl. No. 17/650,147, Notice of Allowance dated Jul. 26, 2023, 9 pages.
U.S. Appl. No. 17/650,147, Supplemental Notice of Allowability dated Sep. 27, 2023, 2 pages.
U.S. Appl. No. 17/942,493, Non-Final Office Action mailed Aug. 24, 2023, 15 pages.
U.S. Appl. No. 18/167,451, Non-Final Office Action mailed Sep. 7, 2023, 21 pages.
Anna, "Ohhio Braid/Unique Chunky Creations", Kickstarter.com, Available online at https://www.Kickstarter.com/projects/1163965827/ohhio-braid-unique-craft-material-for-chunky-creat/creator_bio, Dec. 22, 2021, 2 pages.
Australian Patent Application No. AU2019381647, First Examination Report dated Apr. 26, 2023, 4 pages.
Canadian Patent Application No. CA3105535, Office Action dated Mar. 10, 2021, 4 pages.
Canadian Patent Application No. CA3160008, Notice of Allowance dated Aug. 2, 2022, 1 page.
Chinese Patent Application No. 201980083401.9, Notice of Decision to Grant dated Dec. 14, 2022, 6 pages.
Chinese Patent Application No. CN201980083401.9, Office Action dated May 25, 2022, 10 pages.
Dieuwke, A blanket as a family project, https://knitterskitchen.com/en/2014/10/31/a-blanket-as-a-family-project/, Oct. 31, 2014 (11 pages).
European Patent Application No. EP19884207.2, Extended European Search Report dated Jul. 26, 2022, 8 pages.
European Patent Application No. EP19884207.2, Office Action dated May 17, 2023, 5 pages.
Indian Patent Application No. IN202117026603, First Examination Report dated Mar. 10, 2022, 6 pages.
Lee, "Heat Transfer of Fibrous Insulation Battings", Technical Report TR 84/05, Jan. 1984, Available Online at: https://apps.dtic.mil/sti/pdfs/ADA161032.pdf, 39 pages.
International Patent Application No. PCT/UA2017/000003, International Search Report and Written Opinion dated Sep. 8, 2017, 10 pages.
International Patent Application No. PCT/US2019/055194, International Search Report and Written Opinion dated Dec. 27, 2019, 6 pages.
International Patent Application No. PCT/US2019/055194, International Preliminary Report on Patentability dated May 27, 2021, 6 pages.
International Patent Application No. PCT/US2020/049659, International Search Report and Written Opinion dated Feb. 3, 2021, 17 pages.
Quig, "Properties of Bubblfil", Textile Research, Jan. 1, 1943, pp. 8-12, vol. 13, Issue 3.
Unikatissima, "Clothesline Knitting or Filled I-cord", Available online at: http://www.unikatissima.de/e/?p=2356, Jun. 2, 2009, 6 pages.
Yan, "How to Knit Your Own Chunky Blanket with Your Hands", Mashable.com, Available online at https://mashable.com/video/how-to-knit-your-own-chunky-blanket, Feb. 26, 2017, pp. 1-6.
U.S. Appl. No. 18/526,797, "Non-Final Office Action", Feb. 5, 2024, 11 pages.
U.S. Appl. No. 18/526,797, "Final Office Action", mailed May 24, 2024, 14 pages.
Rabideau, Camryn, "This hand-knit weighted blanket looks beautiful—is it really worth it?", Mar. 14, 2023, retrieved online at: https://www.reviewed.com/home-outdoors/features/bearaby-napper-weighted-blanket-review-does-it-work (Year: 2023).
Blackwell et al., "The Best Weighted Blankets", Sep. 11, 2023, retrieved at: https://www.nytimes.com/wirecutter/reviews/best-weighted-blankets/#a-chunky-knit-weighted-throw-bearaby-cotton-napper (Year: 2023).
Gushue, Jen, "This chunky weighted blanket by Bearaby is one of the few I've found that actually looks nice on my couch", Oct. 26, 2021, retrieved at: https://www.businessinsider.com/guides/home/bearaby-napper-weighted-blanket-review (Year: 2021).
Winfrey, Graham, "How My Company Went From a Garage to an IPO in Under a Decade—and Yours Can Too", May/Jun. 2022,

(56) References Cited

OTHER PUBLICATIONS retrieved at: https://www.inc.com/magazine/202205/graham-winfrey/boxed-chieh-huang-bearaby-kathrin-hamm.html (Year: 2022).

The Lead, "The Lead Foremost 50 2023," retrieved at: https://web.archive.org/web/20230125150714/https://the-lead.co/the-foremost-50-2023/ (Year: 2023).

Clubmental.com, "Best of Mental Health 2022: Don't Tell Me to Calm Down (But I Probably Should)", Mental Editors, Dec. 7, 2022, retrieved at: https://clubmental.com/best-of-mental-health-2022-calm/ (Year: 2022).

PTPA Awards, "Parent Tested Parent Approved announces product award winners for 2022 holiday season", Nov. 15, 2022, retrieved at: https://www.ptpaawards.com/blog/parent-tested-parent-approved-announces-product-award-winners-for-2022-holiday-season/ (Year: 2022).

Fountain, Lauren, "Best Weighted Blanket for Kids", Jan. 27, 2022, retrieved at: https://web.archive.org/web/20220201021126/https://www.sleepfoundation.org/best-weighted-blankets/best-weighted-blanket-for-kids (Year: 2022).

Fountain, Lauren, "Best Cooling Weighted Blankets", Jan. 27, 2022, retrieved at: https://web.archive.org/web/20220218185824/https://www.sleepfoundation.org/best-weighted-blankets/best-cooling-weighted-blankets (Year: 2022).

Fountain, Lauren, "Best Weighted Blankets of 2022", Feb. 11, 2022, retrieved at: https://web.archive.org/web/20221102060400/https://www.sleepfoundation.org/best-weighted-blankets (Year: 2022).

Lam, Jackie, "The Women's Health 2022 Healthy Sleep Awards Winners Are Here", Sep. 13, 2022, retrieved at: https://www.womenshealthmag.com/health/a40906985/healthy-sleep-awards-2022/ (Year: 2022).

Gollayan et al., "The 2022 Men's Health Sleep Awards", Sep. 9, 2022, retrieved at: https://www.menshealth.com/technology-gear/a41068241/mens-health-sleep-awards-2022/ (Year: 2022).

Inc.com, "2022 Inc 5000", Bearaby Profile, retrieved at: https://www.inc.com/profile/bearaby (Year: 2022).

Bowie, Rachel, "The 14 Best Kids' Bedding Brands (Whether You're in the Market for Crib Sheets or a Duvet)", Jun. 1, 2021, retrieved at: https://www.purewow.com/family/best-kids-bedding-brands (Year: 2021).

Chong et al., "The 2021 Men's Health Sleep Awards", Sep. 23, 2021, retrieved at: https://www.menshealth.com/technology-gear/g37399439/mens-health-sleep-awards-2021/?slide=8 (Year: 2021).

PTPA, "Nappling", Parent Tested Product Approved, Online reviews, Aug. 2021, retrieved at: https://www.ptpa.com/product/nappling?quantityPerPage=all&reviewType=t&col=rating&d=desc (Year: 2021).

Tandon, Neha, "Women's Health 2021 Healthy Sleep Awards", Jun. 29, 2021, retrieved at: https://www.womenshealthmag.com/health/a36806140/healthy-sleep-awards-2021/ (Year: 2021).

Sachs, Lexie, "Good Housekeeping's 2021 Best Bedding Awards", May 17, 2021, retrieved at: https://www.goodhousekeeping.com/home-products/a36120685/bedding-awards-2021/ (Year: 2021).

Varghese, Daniel, "The GQ 2021 Home Awards", May 4, 2021, retrieved at: https://www.gq.com/story/gq-home-awards-2021 (Year: 2021).

Segran, Elizabeth, "This weighted blanket will soothe your anxiety (and help the planet)", Sep. 30, 2020, retrieved at: https://www.fastcompany.com/90547626/bearaby-tree-napper-innovation-by-design-2020 (Year: 2020).

Red-Dot, "reddot winner 2020", retrieved at: https://www.red-dot.org/project/tree-napper-44929.

\* cited by examiner

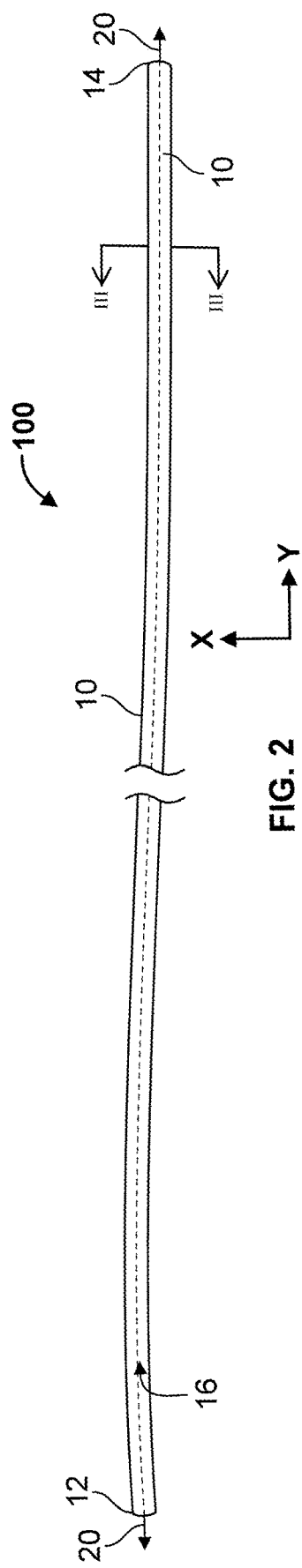
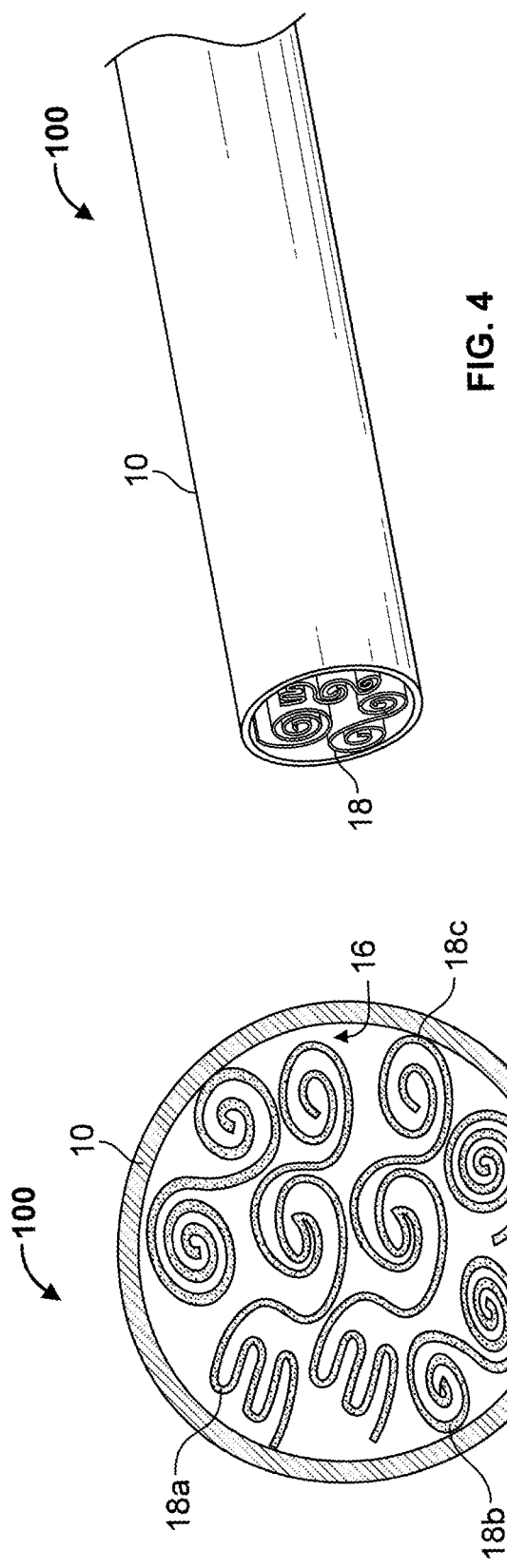
FIG. 2
FIG. 4
FIG. 3

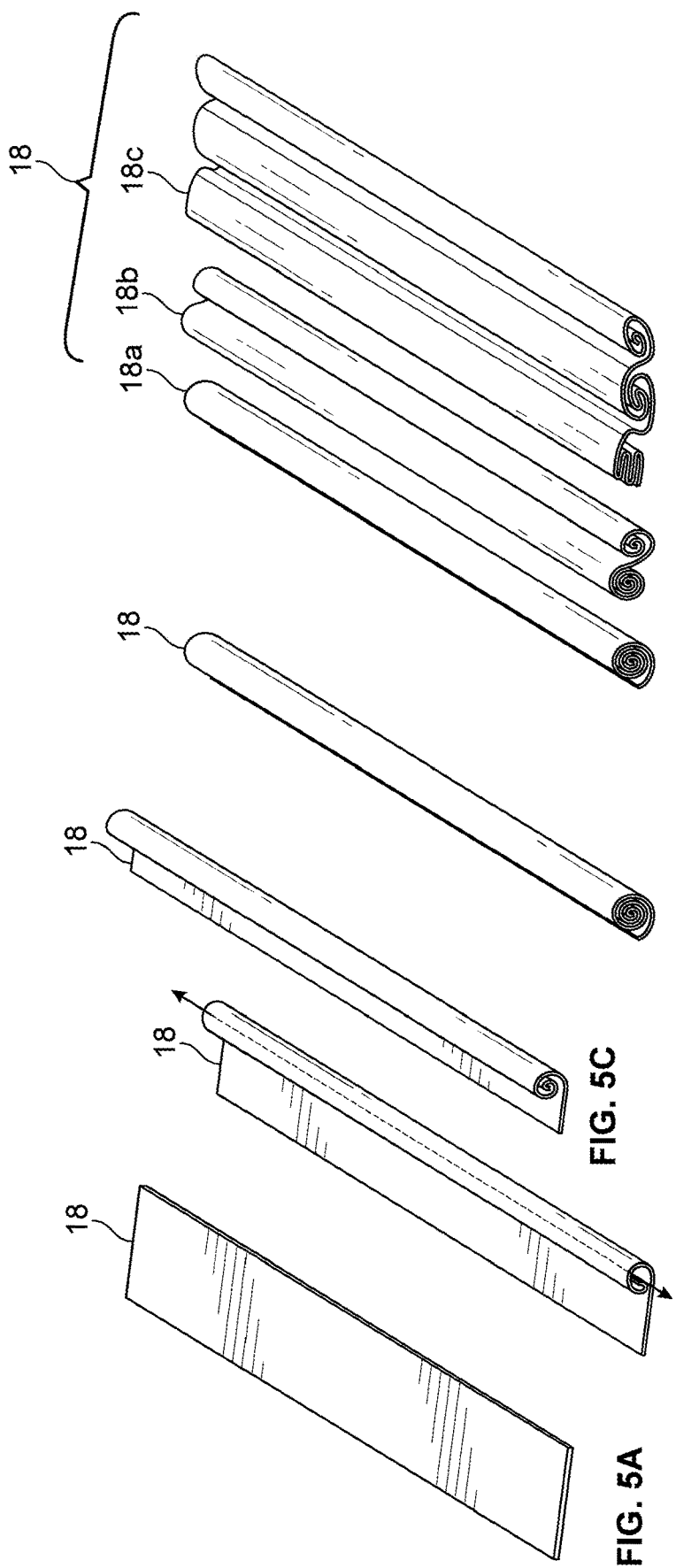

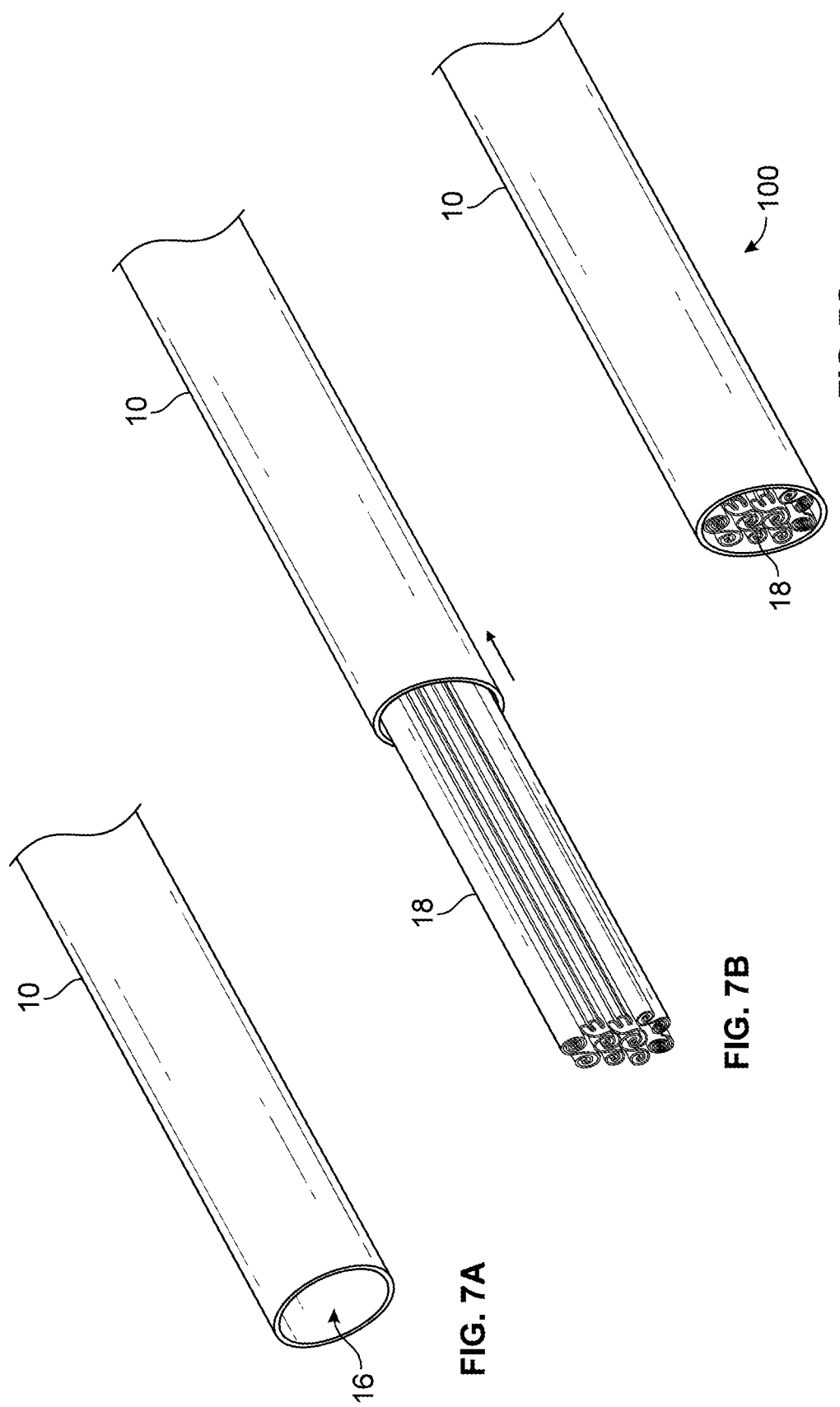

LAYERED YARN AND WEIGHTED BLANKET FOR DEEP PRESSURE THERAPY

CROSS-REFERENCE TO RELATED APPLICATIONS

This application is a continuation of co-pending U.S. patent application Ser. No. 17/650,147, filed Feb. 7, 2022, which is a continuation of U.S. patent application Ser. No. 17/099,033, filed Nov. 16, 2020 and issued as U.S. Pat. No. 11,260,199, which is a continuation of U.S. patent application Ser. No. 16/193,792, filed Nov. 16, 2018 and issued as U.S. Pat. No. 10,835,708, all of which are incorporated herein by reference in their entireties.

BACKGROUND

This disclosure is directed generally to a weighted material that can be used as a weighted blanket to provide a person with deep pressure therapy. It is widely accepted in the medical community that deep pressure therapy may bring relief to those suffering from various disorders, such as insomnia, anxiety, and sensory disorders. Some techniques of deep pressure therapy involve placing across the body a blanket that has weights in it to apply pressure, stimulating a feeling of safety that is also experienced as being hugged or swaddled. In order to be effective, the blanket needs to weigh between about 10-20% of the person's body weight, leading to the blanket weighing between about 5 and 45 pounds.

Conventional deep pressure therapy blankets are typically weighted blankets that are made of a plurality of fabric layers with added weighted materials disposed between the layers. The added weighted materials typically include, for example, plastic pellets or balls, glass beads, sand, gravel, or linked chain objects. The added weighted materials are usually placed in units inside the blanket, for example, quadratic patches that are sewn or stitched to hold the weights. In these conventional approaches, the added materials are required to provide weight because conventional fabric and multiple layers of fabric are not heavy enough to effectively provide deep pressure therapy when placed on a person.

The need for the added weights, however, carries with it several disadvantages. For example, the added weights limit breathability. The added weights and the multiple layers of fabric reduce natural airflow through the blanket. This makes it particularly difficult to regulate the body temperature of an individual when the blanket is placed on them.

As another example, the added weights are prone to moving and shifting with the blanket. This substantially impairs equal, even, and continuous weight distribution, which is needed to effectuate deep pressure therapy. Also, the added weights typically cause the blanket to be overly thick and less bendable, preventing the blanket from naturally taking the body shape of a person lying under it and thereby diminishing the surface contact area of the pressure therapy.

Needed is a weighted material that can be used as a blanket to effectively produce deep pressure therapy to an individual, without the need for additional weight materials.

SUMMARY

As will be described in greater detail below, the instant disclosure describes a weighted blanket that is configured to effectuate deep pressure therapy, without the need for external weights.

In one example, a weighted material is provided. The weighted material is configured to effectuate deep pressure therapy to a person when a piece of the weighted material is used as a blanket over the person's body. A length of layered yarn is interlooped to form the piece of weighted material. The layered yarn includes an outer tube extending longitudinally from a first end to a second end. The outer tube defines a conduit extending longitudinally therethrough from the first end to the second end. A plurality of inner layers of material are disposed within the conduit and extend longitudinally from the first end to the second end. The interlooped length of yarn creates a weighted blanket that is configured and sufficiently weighted to effectuate, by itself, deep pressure therapy to a person when the blanket lies over the person's body. Various other systems and methods are also disclosed.

Features from any of the above-mentioned embodiments may be used in combination with one another in accordance with the general principles described herein. These and other embodiments, features, and advantages will be more fully understood upon reading the following detailed description in conjunction with the accompanying drawings and claims.

BRIEF DESCRIPTION OF THE DRAWINGS

The accompanying drawings illustrate a number of exemplary embodiments and are a part of the specification. Together with the following description, these drawings demonstrate and explain various principles of the instant disclosure.

FIG. 2 is a side view of a layered yarn that can be interlooped to construct the weighted material of FIG. 1, according to an embodiment.

FIG. 3 is a cross-sectional view of the layered yarn of FIG. 2 taken across line 111-111, according to an embodiment.

FIG. 4 is a perspective view of the layered yarn of FIG. 2, according to an embodiment.

FIGS. 5A, 5B, 5C, 5D, and 5E show forming inner layers by folding an inner sheet, according to an embodiment.

FIGS. 7A, 7B, and 7C show constructing a layered yarn, according to an embodiment.

Figure 1:
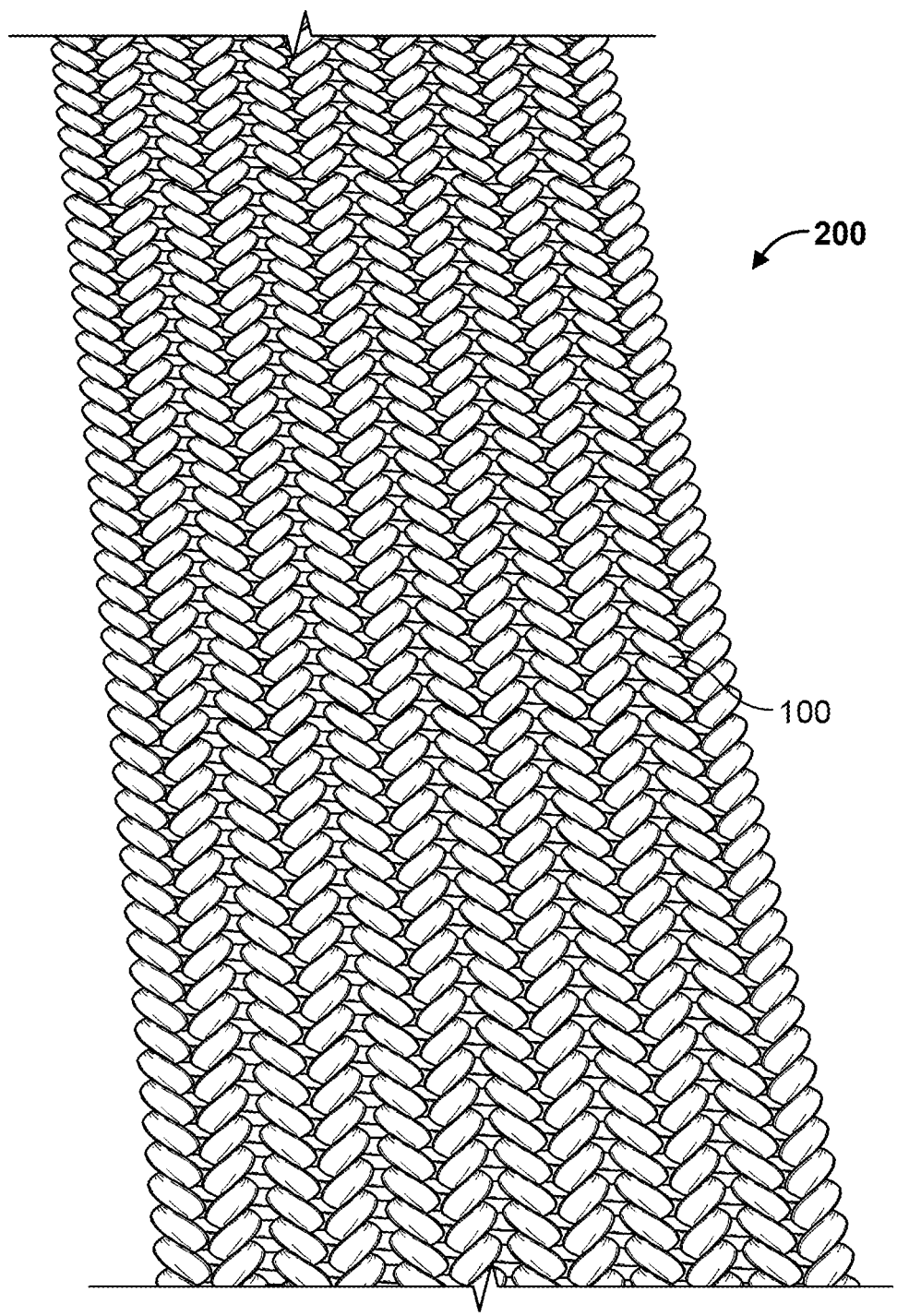
FIG. 1 is a top view of a weighted material comprising a layered yarn that is interlooped, according to an embodiment.

Throughout the drawings, identical reference characters and descriptions indicate similar, but not necessarily identical, elements. While the exemplary embodiments described herein are susceptible to various modifications and alternative forms, specific embodiments have been shown by way of example in the drawings and will be described in detail herein. The exemplary embodiments described herein, however, are not intended to be limited to the particular forms disclosed. Rather, the instant disclosure covers all modifications, equivalents, and alternatives falling within the scope of the appended claims.

DETAILED DESCRIPTION OF EXEMPLARY EMBODIMENTS

The present disclosure is generally directed to a weighted material that can be used as a blanket to provide a person with deep pressure therapy, without the need for weights or components.

As used herein, the terms "providing deep pressure therapy," "bringing about deep pressure therapy" or "effectuating deep pressure therapy" and those similar thereto, refer to effectively causing deep pressure therapy (also known as deep pressure stimulation, deep touch pressure, etc.) in a person as herein described. More particularly, the terms "providing deep pressure therapy," "bringing about deep pressure therapy" or "effectuating deep pressure therapy" and those similar thereto, refer to physically contacting an individual to effectively cause the individual's nervous system activity to switch from being dominated by their sympathetic nervous system to being dominated by their parasympathetic nervous system.

An individual's autonomic nervous system (ANS) receives information from the individual's body and environment, and in response thereto, sends signals out to regulate the individual's body and organs. The ANS includes the sympathetic and parasympathetic systems, which work together to help the individual physiologically respond in accordance with the information the ANS receives.

The sympathetic nervous system is often referred to as the "alert" or "fight or flight" response that is elicited during stressful or emergency situations. The parasympathetic nervous system, on the other hand, is responsible for regulating involuntary functions, such as heart rate and blood pressure, and stimulating the digestive tract. It brings a sense of calm and peace to the mind and body. When the parasympathetic nervous system takes over, an individual's heart rate slows, muscles relax, and circulation improves. When deep pressure is correctly applied, it relaxes the nervous system, causing the body to switch from running its sympathetic nervous system to its parasympathetic nervous system.

Deep touch pressure may also alter the person's hormone levels by decreasing their level of cortisol (which causes and anxiety) while increasing their levels of serotonin and dopamine (which help with mood regulation and relaxation).

The disclosed systems and methods include a weighted material 200 that provides a person with tactile sensory input, which provides proprioceptive input to the individual's body. The weighted material 200 is configured such that when it is administered as a blanket to cover an individual's body, it brings about deep pressure therapy, thus causing the individual's parasympathetic system to increase and their sympathetic system to decrease.

FIG. 1 is a top view of a piece of weighted material 200 comprising a layered yarn 100 that is interlooped (e.g., knit, crocheted, etc.), according to an embodiment. The construction of the layered yarn 100, together with the interlooping thereof, provides a material 200 that is sufficiently heavy to provide deep pressure therapy (DPT) to a person without the need for additional weights. The weighted material 200 is configured so that the interlooped layered yarn 100 (e.g., one layer of the interlooped layered yarn 100), by itself and without any added weights or components, brings about deep pressure therapy in an individual, when the weighted material 200 is employed as a blanket over the individual.

As will be described in further detail below, the disclosed weighted material 200 can be employed as a deep pressure therapy blanket that provides many advantages that are not provided by conventional deep pressure therapy blankets. For example, the disclosed weighted material 200 comprises layered yarn 100 that is interlooped in a pattern that creates small openings at the crossing of the loops. This allows for even airflow through the blanket, thus providing desirable breathability and helping to regulate the person's body temperature.

The interlooping of the layered yarn 100 creates heavy knots at the cross-sections of the loops. This pattern of heavy knots, in turn, creates a pattern of pressure regions on the individual when the weighted blanket 200 is placed over them. This provides a highly effective deep pressure therapy blanket.

Also, the disclosed weighted material 200 offers even weight distribution. The layered yarn 100 may be evenly interlooped (e.g., knit, crochet) in equally sized, enmeshed loops, which distributes the weight substantially equally across the structure of the weighted material 200. The layered yarn 100 is sufficiently heavy and is fixated through the wide-looped pattern.

Thus, unlike conventional DPT blankets, the weight does not shift throughout the structure of the weighted material 200 when the weighted material 200 moves. This is highly advantageous, as continuously maintaining an even weight distribution across the individual is imperative to the efficacy of deep pressure therapy.

Also, the disclosed weighted material 200 provides improved body-contouring abilities. The stretchability of the interlooped layered yarn 100 may take a natural body contouring shape and can adapt to each individual body shape, thus creating a direct and increased surface area for the weight to apply gentle and even pressure across the body. Several other benefits and advantages may be recognized as well.

FIG. 1 shows an embodiment of a weighted material 200 that is constructed by interlooping layered yarn 100 through a knitting technique. Additionally or alternatively, other suitable techniques of interlooping the layered yarn 100 (e.g., crocheting, looping, etc.) may be implemented to form the weighted material 200 while remaining within the scope of this invention. For example, FIG. 9B show a piece of weighted material 200 that is constructed by interlooping the layered yarn 100 through a crocheting technique.

The piece of weighted material 200 shown in FIG. 1 can be utilized as a blanket, for example, for covering a large percentage (e.g., a majority) of a person's body when the person is lying down. In some embodiments, a blanket comprising only a single layer of the weighted material 200 provides sufficient weight to effectuate deep pressure therapy on the person. For example, the weighted material 200 may have a length, width, and height; and the layered yarn 100 may have a longitudinal length and a diameter perpendicular thereto. The height of the weighted material 200 may be equal to the diameter of the layered yarn 100. In other words, the weighted material 200 may consist of only a single layer of the interlooped layered yarn 100 that is sufficiently weighted to effectuate deep pressure therapy when placed over the person's body.

FIGS. 2-4 are side, cross-sectional, and perspective views of a length of layered yarn 100, according to an embodiment. The term yarn, as used herein, refers to a continuous strand of material that can be manipulated (e.g., interlooped) to form a fabric. The layered yarn 100 may be interlooped to provide a piece of weighted material, for example, the piece of weighted material 200 shown in FIG. 1. The layered yarn 100 comprises an outer tube 10 and a plurality of inner layers 18. The outer tube 10 and the inner layers 18 are made from textile material, further details of which are provided below with reference to FIGS. 3 and 4. The outer tube 10 extends longitudinally from a first end 12 to a second end 14. While FIG. 2 shows an embodiment in which the first end 12 and second end 14 are separated from one another, in other embodiments, the length of yarn 100 may comprise a loop, in which the first end 12 and the second end 14 are connected to each other.

The outer tube 10 defines a conduit 16 that extends longitudinally therethrough, from the first end 12 to the second end 14. A plurality of inner layers 18 of material are disposed within the conduit 16 and extend longitudinally from the first end 12 to the second end 14.

The inner layers 18 may be formed by folding at least one inner sheet 18 about at least one fold axis extending substantially longitudinally from the first end 12 to the second end 14. The inner layers 18 may be configured to provide equal weight distribution along the longitudinal length of the layered yarn 100. The inner sheets 18 may be folded longitudinally in any suitable configuration. One or more of the inner sheets 18 may be folded about its respective fold axis a plurality of rotations to provide a coil shape. In some embodiments, the inner sheet is folded about a plurality of fold axes, each of plurality of fold axes extending longitudinally. The inner layers 18 may comprise any suitable number of folded inner sheets 18, such as one to twenty folded inner sheets 18, for example, one to four folded inner sheets 18.

As shown in FIGS. 3 and 4, the inner sheet 18 is folded onto itself into one or more coiled or otherwise folded configuration. As shown in FIGS. 3 and 4, the plurality of inner sheets 18 can each be folded in various fold arrangements. For example, FIG. 3 shows inner sheet 18a that is folded about one respective fold axis in a plurality of rotations to provide a coil shape. FIG. 3 also shows inner sheet 18b that is folded about two respective fold axes in a plurality of rotations to provide two coil shapes. The fold arrangements shown and described herein are exemplary, and the inner layers 18 may comprise any suitable fold arrangement while remaining within the scope of this disclosure.

The fold axis may extend substantially longitudinally from the first end 12 to the second end 14, so that the inner sheet is folded onto itself lengthwise. The fold axis, however, does not need to be entirely straight or parallel to the longitudinal axis of the layered yarn 100. For example, the folded inner sheet 18 may be twisted or squished along the length of the layered yarn 100.

The plurality of inner layers 18 may extend uninterrupted along the longitudinal length of the layered yarn 10. For example, the at least one folded inner sheets 18 may be uninterrupted along the longitudinal length (e.g., extending uninterrupted from the first end 12 to the second end 14 of the layered yarn 100). This may provide a layered yarn 100 having a substantially homogeneous weight distribution along its length, which in turn may provide a weighted material 200 that has a substantially homogeneous weight distribution across its surface.

The plurality of inner layers 18 may be disposed within the conduit 16 and fill the conduit 16 of the hollow tube 10 by any suitable proportion. For example, the folded inner sheets 18 may take up between about 75-99% of the volume of the conduit 16. For example, the folded inner sheets 18 may take up between about 85-95% of the volume of the conduit 16. For example, the folded inner sheets may take up between about 90% of the volume of the conduit 16. The inner layers 18 may be configured to take up enough volume within the conduit to provide sufficient weight, while allowing for sufficient air flow to flow through the layered yarn 100.

The outer tube 10 and inner layers 18 may be made of any suitable textile materials, for example, spun and/or woven fibers. The outer tube 10 and/or inner layers 18 may be made out of cotton, for example, organic cotton (e.g., entirely made of 100% organic cotton). The outer tube 10 and/or inner layers 18 may include a material that demonstrates high stretching properties, such as elastane, to facilitate interlooping the yarn 100.

In some embodiments, the outer tube 10 is made of a cotton-elastane mix, and the inner layers 18 are made almost entirely (e.g., entirely) of cotton (e.g., entirely made of 100% organic cotton). This construction provides a layered yarn 100 that demonstrates sufficient stretchability (from the elastane material in the outer tube) to facilitate interlooping of the layered yarn 100 and body contouring of the weighted material 200, while also maintaining sufficient rigidity (from the cotton in the outer tube, and the cotton inner layers) to provide steady weight distribution of the blanket 200.

The weighted material 200 may have any suitable dimensions to be employed as a blanket over a person laying down to bring about deep pressure therapy. For example, the weighted material 200 may have a length between 50 and 80 inches, for example, between 65 and 75 inches. The weighted material 200 may have a width between about 35 and 70 inches, for example, between 45 and 55 inches. In some embodiments, a piece of material 200 is about 48 inches wide, 72 inches long, and 2 inches high, and is made of a length of interlooped layered yarn 100 that is about 250 meters long and that has a diameter of about 2 inches.

The weighted material 200 may be configured to weigh between 5 lb. and 45 lb. for example, between 7 lb. and 40 lb., for example, between 10 and 35 lb. The weighted material 200 may weigh between about 10% and 20% of a person's body weight, and the weighted material 200 may be configured to bring about deep pressure therapy for a person weighing between, for example, 35 lb. and 400 lb. In some embodiments, the piece of weighted material 200 has dimensions of about 48×72×2 inches, weighs between 20 and 35 lb., and is constructed from a length of interlooped layer yarn that is about 250 meters long and has a diameter of about 2 inches.

The layered yarn 100 may have a diameter between about 1 and 5 inches. For example, the layered yarn 100 may have a diameter between about 1.5 and 3 inches. In some embodiments, the layered yarn 100 has a diameter of about 2 inches. In some embodiments, the plurality of inner layers 18 comprise folded inner sheets 18 that have a length that is substantially the same as the length of the hollow tube 10, and the inner sheets 18 have a width that is greater than the diameter of the hollow tube 10.

FIGS. 5A-5E show a schematic representation of forming inner layers 18 by folding an inner sheet 18, according to an embodiment. FIG. 5A shows an inner sheet 18 that is in a substantially flat configuration. The inner sheet 18 shown in FIG. 5A may be formed of a larger sheet 18 that is folded along one or more fold lines to provide the substantially flat configuration shown in FIG. 5A. FIGS. 5B and 5C show the inner sheet 18 of FIG. 5A as it is being rolled along the longitudinally extending fold axis. FIG. 5D shows the inner sheet 18 of FIGS. 5A-5C that is rolled along the longitudinally extending fold axis. FIG. 5E shows the inner sheet 18a of FIGS. 5A-5D, together with additional inner sheets 18*b*, 18*c* that are each folded along their respective longitudinally extending fold axes. The inner sheets 18 can be arranged within the hollow tube 10 to form the layered yarn 100.

Figure 6B:
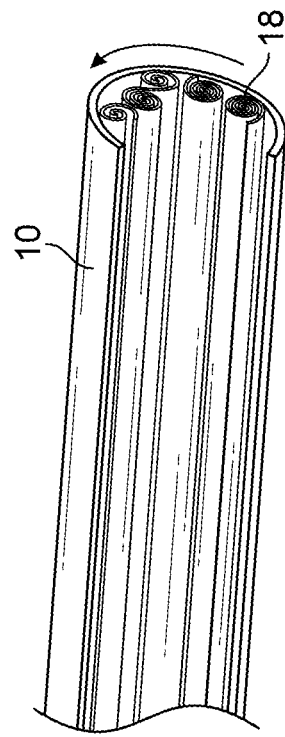
FIGS. 6A, 6B, and 6C show constructing a layered yarn, according to an embodiment.
Figure 6A:
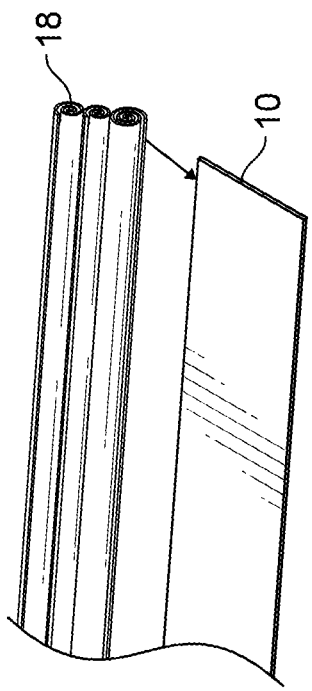
Figure 6C:
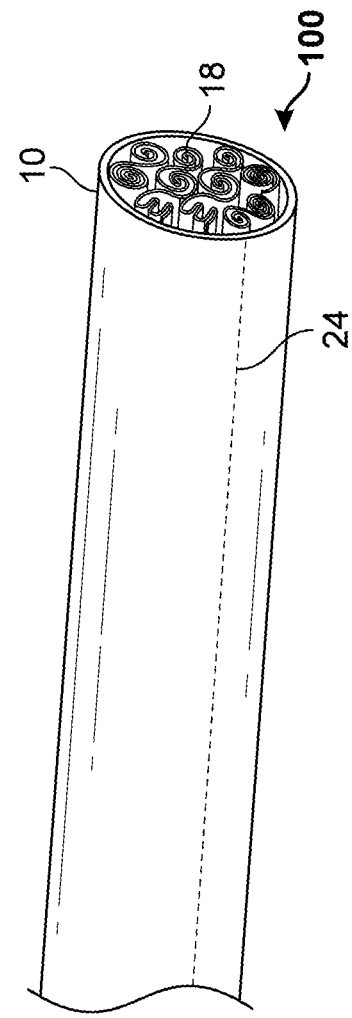

FIGS. 6A-6C show a schematic representation of constructing a layered yarn 100, according to an embodiment. FIG. 6A shows the outer layer 10 that is arranged as a sheet (e.g., sheet of fabric) before it is rolled into the hollow tube 10. Also shown in FIG. 6A is the at least one folded inner layer 18 as it is being arranged on top of the outer sheet 10. FIG. 6B shows the at least one folded inner layer 18 disposed on the outer sheet 10, and the outer sheet 10 being rolled into the hollow tube 10. FIG. 6C shows the hollow tube 10 rolled around the plurality of inner layers 18 to form the layered yarn 100. The outer layer 10 may be attached at seam 24 by any suitable means (e.g., stitching, adhesion, friction, hook-and-loop, etc.) to secure the hollow tube 10. The hollow tube 10 may be attached to itself at ends 12, 14 to close the conduit 16.

FIGS. 7A-7C show a schematic representation of constructing a layered yarn 100, according to an embodiment. FIG. 7A shows the outer tube 10 that is hollow, with conduit 16 extending longitudinally therethrough. In some embodiments, the outer tube 10 is formed by rolling an outer layer sheet 10 and securing it at a seam into a tube shape (e.g., by attaching the rolled sheet by suitable means (e.g., stitching, adhesion, friction, hook-and-loop, etc.) similarly to the attachment seam 24 shown in FIG. 6C. In some embodiments, the outer tube 10 is formed as a seamless tubular structure. For example, the outer tube 10 may be formed by interlocking fibers to form the tubular configuration. FIG. 7B shows the plurality of inner layers 18 being inserted into the conduit 16 of the hollow tube 10. FIG. 7C shows the plurality of inner layers 18 that are arranged inside the hollow tube 10 to provide the layered yarn 100. The hollow tube 10 may be attached to itself at ends 12, 14 to close the conduit 16.

In some embodiments, the plurality of inner layers 18 may be attached together by any suitable means to maintain, for example, the folded configuration. For example, the at least one folded inner sheets 18 may be stitched and/or adhered to itself. Additionally or alternatively, the plurality of inner layers 18 may be attached to at least a portion of the inner tubular wall of the hollow tube 10 by any suitable means. For example, the at least one folded inner sheet 18 may be attached to the inner tubular wall of the hollow tube 10 by way of stitching, adhesion (e.g., glue), friction, hook-and-loop, etc.

Figure 8A:
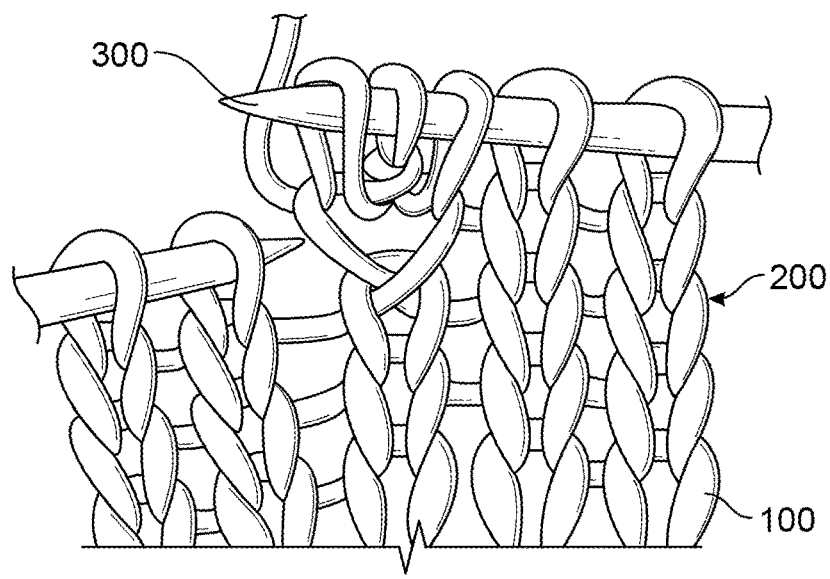
FIG. 8A is a perspective view of layered yarn being knit to construct a piece of weighted material, according to an embodiment.
Figure 9:
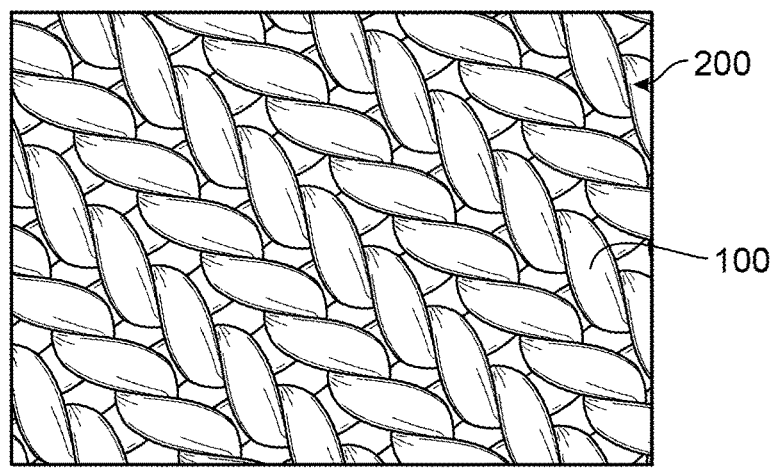
FIG. 9 is a top view of a piece of weighted material that is constructed by knitting layered yarn, according to an embodiment.

FIG. 8A is a perspective view of a layered yarn 100 that is being knit to construct a piece of weighted material 200, according to an embodiment. FIG. 9 is a top view of a piece of weighted material 200 that is constructed by knitting layered yarn 100 (e.g., as shown in FIG. 8A), according to an embodiment. The layered yarn 100 may be knit using a pair of knitting needles 300. The knitting may be performed manually by a user and/or using an automated machine. The knitting may comprise intermeshing loops of the layered yarn 100 in a number of consecutive rows. As each row progresses, a newly generated loop is pulled through one or more loops from the prior row, creating a dense pattern.

Figure 8B:
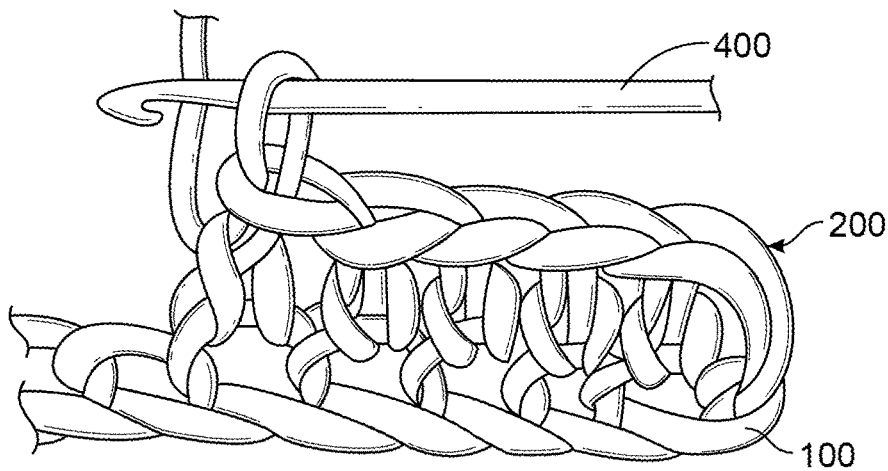
FIG. 8B is a perspective view of a layered yarn being crocheted to construct a piece of weighted material, according to an embodiment.

FIG. 8B is a perspective view of a strand of layer yarn 100 being crocheted to construct a piece of weighted material 200, according to an embodiment. The layered yarn 100 may be crocheted using a pair of crocheting needles 400, as shown. The crocheting may be performed manually by a user and/or using an automated machine. The crocheting may comprise intermeshing loops of the layered yarn 100 in a number of consecutive rows.

As shown in FIGS. 7A and 7B, the weighted material 200 comprises layered yarn 100 that is interlooped in a pattern that creates small openings at the crossing of the loops. This allows for even airflow through the blanket, thus providing desirable breathability and helping to regulate the individual's body temperature. The interlooping of the layered yarn 100 (e.g., knitting as shown in FIG. 8A, crocheting as shown in FIG. 8B), together with the construction of the layered yarn 100, creates a piece of weighted material 200 that is dense enough to provide deep pressure therapy for a person. For example, the piece of weighted material 200 can have dimensions, of about 48×72×2 inches and can weigh between 20 and 35 lb. The interlooped material 200 is both sufficiently wide-looped and dense to effectuate deep pressure therapy, while also providing superior breathability, even and continuous weight distribution, and natural body contouring capabilities.

The interlooping of the layered yarn 100 creates heavy knots at the cross-sections of the loops. This pattern of heavy knots, in turn, creates a pattern of pressure regions on the individual when the weighted blanket 200 is placed over them. This provides a highly effective deep pressure therapy blanket.

FIGS. 8A and 8B show formation of a single layer of interlooped layered yarn 100. For example, the thickness of the weighted material 200 is equal to the diameter of the layered yarn 100. In some embodiments, the layered yarn 100 is sufficiently heavy, and the layered yarn 100 is interlooped such that only a single layer of the interlooped yarn 100 creates a piece of weighted material 200 that, when employed as a blanket over a person, brings about deep pressure therapy to the person.

Figure 10:
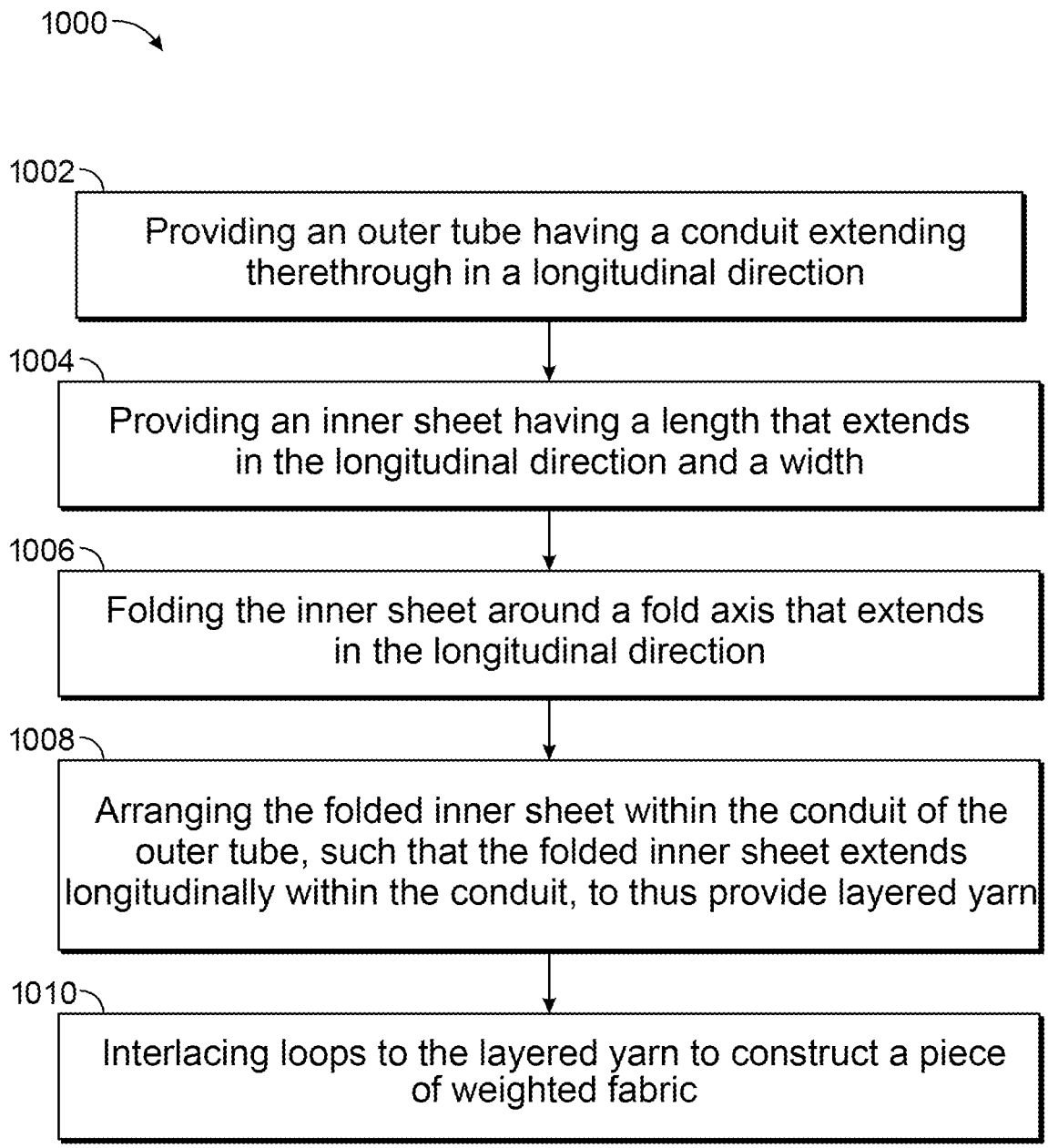
FIG. 10 is a flowchart of an exemplary method of constructing a piece of weighted material, according to an embodiment.

FIG. 10 is a flowchart of a method 1000 of constructing a piece of weighted material, according to an embodiment. In steps 1002-1008, a layered yarn is constructed. At step 1002, an outer tube is provided. The outer tube includes a conduit extending therethrough in a longitudinal direction. At steps 1004 and 1006, an inner sheet is provided and folded around a fold axis, which extends in a longitudinal direction. At step 1008, the folded inner sheet is arranged within the conduit, such that the folded inner sheet extends longitudinally within the conduit. At step 1010, the constructed layered yarn is interlooped to construct a piece of deep pressure therapy material.

The weighted material 200 of FIG. 1 is employed as a blanket over a person's body (e.g., a majority of the person's body). The piece of weighted blanket 200 may be configured to provide sufficient air circulation through the weighted blanket 200 to regulate the body temperature of the person. For example, the weighted blanket 200 may be configured to provide 18-26% air flow therethrough (e.g., from the air above the blanket 200 to the person laying beneath the weighted blanket 200).

The weighted material's 200 beneficial air flow qualities may be provided by the interlooping of the layered yarn 100 (allowing air to circulate around the layered yarn 100) as well as the construction of the layered yarn 100 (allowing air to circulate through the layered yarn 100). For example, as described above with reference to FIGS. 9A and 9B, the weighted material 200 may be created by an interlooped pattern that creates small openings at the crossing of the loops, and between the loops of layered yarn 100. Thus, air flow may travel from the top and to the bottom of the weighted material 200 through the small openings (the air flowing around the layered yarn 100). Also, the layered yarn 100 may be configured to allow air to circulate through the yarn itself. For example, the configuration of the hollow tube 10 and the plurality of layers 18 provide empty spaces within the conduit 16. Air is thus allowed to circulate along the empty spaces and through the conduit 16 (the air flowing through the layered yarn 100). In addition to providing superior air circulation, the construction of the material 200 also provides well-balanced moisture and heat transfer capabilities.

The layered yarn 100 may be configured to have a substantially homogenous weight and density along its longitudinal length. This provides many advantages over strands of material that comprise bunched up filler material. For example, the bunched up filler material creates inconsistent weight distribution, which greatly impairs even weight distribution of the weighted blanket. The layered yarn 100, however, is configured to maintain weight distribution through the interlooping of the yarn 100 and the movement and use of the blanket 200.

While the outer tube 10 and inner layers 18 are shown and described as being separate components, in some embodiments, the outer tube 10 and at least one of the inner layers 18 are integrally formed. In some embodiments, the inner layers 18 are attached (e.g., at a seam along the longitudinal length of the layered yarn 100), so the outer periphery of the attached inner layers 18 forms the outer construction of the yarn (e.g., without a separate outer tube 10).

While this disclosure describes using the piece of weighted material 200 to provide deep pressure therapy, it should be well understood that the weighted material 200 may be used for other purposes, in addition to or as an alternate to deep pressure therapy. Also, while the disclosure describes employing the piece of weighted material 200 as a blanket to lay over an individual, it should be well understood that the weighted material 200 may be employed in other suitable ways. Further, while this disclosure describes laying the piece of material 200 over a person, it should be well understood that the material 200 may be laid over other suitable kinds of animals to provide them with deep pressure therapy.

The preceding description has been provided to enable others skilled in the art to best utilize various aspects of the exemplary embodiments disclosed herein. This exemplary description is not intended to be exhaustive or to be limited to any precise form disclosed. Many modifications and variations are possible without departing from the spirit and scope of the instant disclosure. The embodiments disclosed herein should be considered in all respects illustrative and not restrictive. Reference should be made to the appended claims and their equivalents in determining the scope of the instant disclosure.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of."

Finally, for ease of use, the terms "including" and "having" (and their derivatives), as used in the specification and claims, are interchangeable with and have the same meaning as the word "comprising."

What is claimed is:

1. A weighted blanket comprising:
   a layer of yarn interlooped to create a pattern of regularly spaced openings through the weighted blanket, the weighted blanket having a substantially even weight distribution, wherein the yarn comprises:
   an outer tube formed of a fabric that defines a conduit extending longitudinally through an inside of the outer tube; and
   a filling arranged within the conduit and comprising a plurality of inner fiber layers, each inner fiber layer extending longitudinally through the conduit and having a fiber layer length that is substantially equal to an outer tube length,
   wherein the weighted blanket has a density in a range of between 4.37 pounds per cubic foot and 13.1 pounds per cubic foot, inclusive, and the substantially even weight distribution per square foot in a range of between 0.3 pounds per square foot and 1.5 pounds per square foot, inclusive.

2. The weighted blanket of claim 1, wherein the weighted blanket comprises a height and wherein the height of the weighted blanket is substantially the same as a diameter of the yarn.

3. The weighted blanket of claim 1, wherein the plurality of inner fiber layers comprise at least one of cotton fibers, synthetic fiber, and elastane.

4. The weighted blanket of claim 1, wherein the filling comprises longitudinally folded sheets of material.

5. The weighted blanket of claim 1, wherein the filling occupies about 75%-99%, inclusive, of the conduit.

6. The weighted blanket of claim 1, wherein the filling comprises interlocking inner fiber layers.

7. The weighted blanket of claim 1, wherein the weighted blanket weighs between 5 pounds and 45 pounds, inclusive.

8. The weighted blanket of claim 7, wherein the weighted blanket has a length in a range of between 50 inches and 80 inches, inclusive, a width in a range of between 35 inches and 70 inches, inclusive, and a thickness in a range of between 1 inches and 5 inches, inclusive.

9. The weighted blanket of claim 1, wherein the fabric is a stretch fabric material.

10. The weighted blanket of claim 1, wherein the yarn comprises a diameter in a range of between one and five inches, inclusive.

11. The weighted blanket of claim 1, wherein the weighted blanket has the substantially even weight distribution per square foot in a range of between 0.4 pounds per square foot and 1.2 pounds per square foot, inclusive.

12. The weighted blanket of claim 1, wherein the weighted blanket has the substantially even weight distribution per square foot in a range of between 0.5 pounds per square foot and 1.0 pounds per square foot, inclusive.

13. A weighted blanket comprising:
   a layer formed of a continuous strand tubular yarn interlooped to form a pattern of regularly spaced openings to permit air flow through the weighted blanket,
   wherein the continuous strand tubular yarn comprises:
   an outer tube formed of a fabric and defining a conduit extending longitudinally through an entire length of the outer tube, and
   a filling within the conduit, the filling comprising a plurality of fiber layers, each fiber layer extending longitudinally through substantially the entire length of the outer tube,
   wherein the weighted blanket has a substantially even weight distribution of between 0.3 pounds per square foot and 1.5 pounds per square foot, inclusive.

14. The weighted blanket of claim 13, wherein the weighted blanket has the substantially even weight distribution per square foot in a range of between 0.5 pounds per square foot and 1.0 pounds per square foot, inclusive.

15. The weighted blanket of claim 13, wherein the weighted blanket has the substantially even weight distribution per square foot in a range of between 0.4 pounds per square foot and 1.2 pounds per square foot, inclusive.

16. The weighted blanket of claim 13, wherein the pattern of regularly spaced openings is configured to permit 18-26% air flow through the weighted blanket.

17. The weighted blanket of claim 13, wherein the outer tube comprises a diameter in a range of between one and five inches, inclusive.

18. The weighted blanket of claim 17, wherein the weighted blanket comprises a height and wherein the height of the weighted blanket is substantially the same as the diameter of the tubular yarn.

19. The weighted blanket of claim 13, wherein the filling comprises elastane.

20. The weighted blanket of claim 13, wherein the weighted blanket has a length in a range of between 50 inches and 80 inches, inclusive, and a width in a range of between 35 inches and 70 inches, inclusive.

21. The weighted blanket of claim 13, wherein the weighted blanket has a weight between 5 pounds and 45 pounds, inclusive.

22. The weighted blanket of claim 13, wherein the weighted blanket has a density in a range of between 4.37 pounds per cubic foot and 13.1 pounds per cubic foot, inclusive.

23. A weighted blanket comprising:
only a single layer formed of a continuous strand yarn interlooped to create a pattern of regularly spaced openings through the weighted blanket, wherein the continuous strand yarn comprises:
an outer tube formed of a fabric that defines a conduit extending longitudinally through the outer tube, and
a filling arranged within the conduit, the filling comprising a plurality of fiber layers, each fiber layer extending longitudinally through substantially an entirety of the conduit,
wherein the weighted blanket further comprises:
a substantially even weight distribution per square foot;
a length in a range of between 50 and 80 inches, inclusive;
a width in a range of between about 35 and 70 inches, inclusive; and
a weight between 5 pounds and 45 pounds, inclusive.

24. The weighted blanket of claim 23, wherein the filling comprises a single fabric sheet foiled to form the plurality of fiber layers.

25. The weighted blanket of claim 23, wherein the weighted blanket has the weight distribution per square foot in a range of between 0.5 pounds per square foot and 1.0 pounds per square foot, inclusive.

26. The weighted blanket of claim 23, wherein the weighted blanket has a density in a range of between 4.37 pounds per cubic foot and 13.1 pounds per cubic foot, inclusive.

27. The weighted blanket of claim 23, wherein the weighted blanket has the substantially even weight distribution per square foot in a range of between 0.3 pounds per square foot and 1.5 pounds per square foot, inclusive.

28. The weighted blanket of claim 23, wherein the weighted blanket has the substantially even weight distribution per square foot in a range of between 0.4 pounds per square foot and 1.2 pounds per square foot, inclusive.

* * * * *